United States Patent [19]

Diehl et al.

[11] 3,976,785

[45] Aug. 24, 1976

[54] DIOXOCYCLOHEXANECARBOXANILIDE INSECTICIDES AND ACARICIDES

[75] Inventors: Robert Eugene Diehl, Trenton; Michael Stanley Schrider, South Bound Brook; Sidney Kantor, Lawrenceville, all of N.J.

[73] Assignee: American Cyanamid Company, Stamford, Conn.

[22] Filed: May 15, 1975

[21] Appl. No.: 577,976

Related U.S. Application Data

[60] Continuation-in-part of Ser. No. 412,088, Nov. 2, 1973, abandoned, which is a division of Ser. No. 197,967, Nov. 11, 1971, now Defensive Publication No. 3,801,630, which is a continuation-in-part of Ser. No. 106,933, Jan. 15, 1971, abandoned.

[52] U.S. Cl. .................................................. 424/324
[51] Int. Cl.² ...................... A01N 9/20; A01N 9/12

[58] Field of Search ................................... 424/324

[56] References Cited
UNITED STATES PATENTS 3,801,630    4/1974    Diehl et al. ..................... 260/551 S

OTHER PUBLICATIONS

Ukita et al.–Chem. & Pharm. Bull., (Japan), vol. 8, pp. 1016–1020, (1960).

*Primary Examiner*—Leonard Schenkman
*Attorney, Agent, or Firm*—Harry H. Kline

[57] ABSTRACT

The present invention relates to certain carboxanilide insecticidal and acaricidal methods and compositions. It further relates to certain carboxanilides employed as active ingredients therein.

15 Claims, No Drawings

DIOXOCYCLOHEXANECARBOXANILIDE INSECTICIDES AND ACARICIDES

This application is a continuation-in-part of our co-pending divisional application, Ser. No. 412,088 filed on Nov. 2, 1973, now abandoned, which in turn is a divisional of Ser. No. 197,967, filed on Nov. 11, 1971, now U.S. Pat. No. 3,801,630, issued on Apr. 2, 1974, which patent is a continuation-in-part of Ser. No. 106,933, filed on Jan. 15, 1971, now abandoned.

The present invention relates to certain novel carboxanilides. It further relates to the use of certain known carboxanilides and the novel carboxanilides as insecticides and acaracides. It further relates to the synthesis of the carboxanilides through the reaction of a 1,3-cyclohexanedione with a phenylisocyanate or phenylisothiocyanate.

The carboxanilides useful as insecticides and acaracides in the present invention may be represented by the following structure:

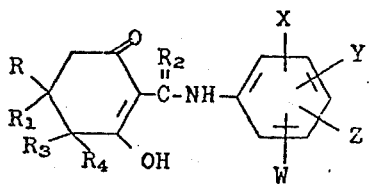

wherein R and $R_1$ are each selected from the group consisting of hydrogen, lower alkyl ($C_1$–$C_4$), phenyl, halophenyl, and benzyl; $R_2$ is sulfur or oxygen; $R_3$ and $R_4$ are each selected from the group consisting of hydrogen, lower alkyl ($C_1$–$C_4$) and phenyl; W is hydrogen or halogen; X is hydrogen, halogen, lower alkyl ($C_1$–$C_4$), halo-substituted lower alkyl ($C_1$–$C_4$), lower alkoxy ($C_1$–$C_4$), lower alkylthio ($C_1$–$C_4$), or nitro; Y is hydrogen, halogen, lower alkyl ($C_1$–$C_4$) or halo-lower alkyl ($C_1$–$C_4$); and Z is hydrogen or halogen.

Suitable lower alkyl substituents include, for example, methyl, ethyl, n-propyl, iso-propyl, n-butyl, sec-butyl groups. The corresponding alkoxy and alkylthio groups are also suitable for use in the present invention. Suitable halogen substituents include, for example, fluoro, chloro, bromo and iodo groups. Suitable lower carbalkoxy groups include, for example, carbomethoxy, carbethoxy, carbopropoxy and carbobutoxy groups.

Suitable halo substituted lower alkyl groups include, for example, ennechlorobutyl, heptachloropropyl, 2,2,2-trichloroethyl, 2,2,2-tribromoethyl, 2,2-dichloroethyl, 2-fluoroethyl, 2-bromoethyl, 2-chloroethyl, chlorodifluoromethyl, chloromethyl, bromomethyl, fluoromethyl, and the like. Of the numerous suitable halo substituted lower alkyl substituents, a few of which are mentioned above, the trihalomethyl substituents are especially preferred. Within this preferred group one may mention trichloromethyl and trifluoromethyl as being especially preferred.

Suitable halophenyl groups include, for example, the ortho and para, mono and disubstituted bromo and chlorophenyl groups. Parachlorophenyl substituents are among the preferred.

The carboxanilides which are employed in the pesticidal methods of the present invention have the formula:

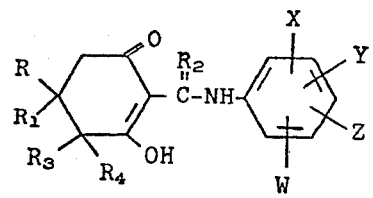

wherein R and $R_1$ are each selected from the group consisting of hydrogen, phenyl, halophenyl, benzyl and lower alkyl ($C_1$–$C_4$); $R_2$ is sulfur or oxygen; $R_3$ and $R_4$ are each selected from the group consisting of hydrogen, lower alkyl ($C_1$–$C_4$) and phenyl; W is hydrogen or halogen; X is hydrogen, halogen, lower alkyl ($C_1$–$C_4$), halo-substituted lower alkyl ($C_1$–$C_4$), lower alkoxy ($C_1$–$C_4$), lower alkylthio ($C_1$–$C_4$), cyano, carb-lower alkoxy ($C_1$–$C_4$) or nitro; Y is hydrogen, halogen, lower alkyl ($C_1$–$C_4$) or halo-lower alkyl ($C_1$–$C_4$) and when X and Y are taken together they can form a benzo group; and Z is hydrogen or halogen. Known carboxanilides within this class are discussed, for example, by N. Rogers et al., J. Chem. Soc., page 341(1955) and by T. Ukita et al., Chem. Pharm. Bull. (JAP), 8, 1016-20(1960).

The synthetic process for the preparation of the curboxanilides employed in the pesticidal process involves the reaction of a 1,3-cyclohexanedione with a phenylisocyanate or a phenylisothiocyanate. The reaction is generally carried out in the presence of a tertiary organic amine, with or without an organic solvent. Elevated temperatures are generally employed to facilitate the reaction. Temperatures in the range of from about 30°C. to about 150°C. are generally suitable, with temperatures in the range of from about 50°C. to about 100°C. being preferred. Following the period of heating, which will usually be under reflux, the carboxanilide may be precipitated by the addition of an aqueous solution of mineral acid. The product may then be recovered from the mixture by any convenient means, as, for example, by filtration, centrifugation or the like. If desired, purification can be effected by redissolving the product in a solvent of moderate polarity, such as ethyl ether, a $C_1$–$C_4$ alcohol, cyclohexane, methylene chloride, or the like and filtering off the insoluble material. The desired carboxanilide can be recovered from the filtrate by evaporation. This synthetic reaction scheme may be graphically illustrated as follows:

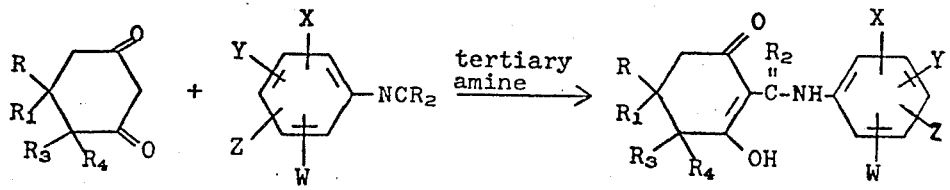

The isocyanates and isothiocyanates employed in the preparation of the carboxanilides may be conveniently prepared from the appropriate anilides by reaction with phosgene or thiophosgene. Typical procedures for these general reactions are set forth by S. Petersen et al., Chemische Berichte, 81, page 31–8(1948), C.A., 43, page 169a; E. Dyer et al., JACS, 54, 777/87(1932); Wagner and Zook, Synthetic Organic Chemistry, pages 640 and 827–30, John Wiley & Sons, Inc. (1953).

For use as insecticides or acaricides, the carboxanilides are formulated and applied by conventional methods to the foliage of plants to protect them from pests which feed thereon, or to the soil to protect plants from soil-borne pests as well as warm-blooded animals, such as farm, domestic, zoo and laboratory animals, to protect them against and/or rid them of insect and acarid infection. They may also be applied to breeding sites of the insects and acaricides to control the egg, larvae and adult stages of breeding pest populations. In this regard, 4'-chloro-2-hydroxy-6-oxo-1-cyclohexene-1-carboxanilide is preferred as a larvicidal and ovicidal agent for the control of insects and acarids. These compounds are advantageously formulated as dusts, dust concentrates, emulsifiable liquids, wettable powders and the like.

The dusts are usually prepared by simply grinding together from about 1% to 15% by weight of the active carboxanilide with a finely divided inert diluent such as walnut flour, diatomaceous earth, fullers earth, atta-clay, talc, or kaolin. Dust concentrates are made in similar fashion, excepting that about 16% to 75% by weight of active ingredient is ground together with the diluent. In practice, this concentrate is then generally admixed at the site of use with more inert diluent before it is applied to the plant foliage or animals which are to be protected from insect and acarid attack.

Wettable powders are generally prepared in the same manner as dust concentrates, but usually about 1% to 5% by weight of a dispersing agent, for example an alkali metal lignosulfonate and about 1% to 5% of a surfactant, such as alkyl phenoxy polyethylene ethanol, naphthalene sulfonic acid condensate, or an ester of sodium isothionate, is incorporated in the formulation. For application to agronomic crops, shrubs, ornamentals, and the like, the wettable powder is usually dispersed in water and applied as a spray. For treatment of warm-blooded animals, the same spray type application may be used or the wettable powder may be dispersed in the water of a dipping trough through which the animals are driven.

The emulsifiable liquids may be prepared by dissolving the active compound in an organic solvent, such as acetone, and admixing the thus formed solution with other organic solvents, such as cyclohexanone and toluene containing an emulsifier such as calcium dodecylbenzene sulfonate or an alkylaryl polyether alcohol. The emulsifiable liquid is then generally dispersed in water for spray or dip application.

In practice, we have found that the compounds of the present invention in which at least one of X, Y or Z represents a substituent other than hydrogen, are preferred for use in controlling acarids. Moreover, we have found the mono-, di-, and trihalosubstituted carboxanilides, particularly the mono-, di- and tri-chloro carboxanilides, are most effective for inhibiting or reducing tick infestations on warm-blooded animals.

The present invention is further illustrated by the examples set forth below which are not to be taken as limitative thereof. In each case, parts are by weight unless otherwise indicated.

EXAMPLES 1–19

Preparation of 3',4'-Dichloro-2-Hydroxy-6-Oxo-1-Cyclohexene-1-Carboxanilide and Related Compounds A solution containing 1,3-cyclohexanedione, 144 parts, 3,4-dichlorophenylisocyanate, 240 parts, in pyridine, 800 parts, is heated at 110°–115°C. for 2 hours. After cooling, the mixture is poured with stirring into a solution containing 2000 parts of concentrated hydrochloric acid in 7500 parts of cold water. A solid formed which is collected and washed on the filter with cold water and dried in a vacuum oven at 50°C. The pure carboxanilide is obtained by crystallization from 7000 parts of ethyl alcohol to give 242 parts of light tan colored crystals, melting point 131°–132°C.

The compounds of Table I having the structure set forth below are prepared by essentially the same procedure as above using the appropriately substituted isocyanate in place of the 3,4-dichlorophenylisocyanate. Reaction periods vary from 2 to 4 hours at temperatures usually of 95°–100°C. In cases where appreciable amounts of substituted carbanilides corresponding to the isocyanates are formed, purification is further effected by dissolving the carboxanilide in a solvent of moderate polarity, such as ethyl ether or methylene chloride, filtering off the insoluble carbanilide, and recovering the product from the filtrate by evaporation of the solvent.

Table I

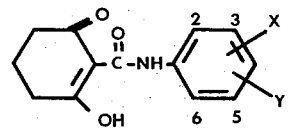

| Example | Substituents X | Y | Melting Point | Calculated C | H | N | Found C | H | N |
|---|---|---|---|---|---|---|---|---|---|
| 2 | 3-Cl | 4-Cl | 131°C.–132°C. | 52.02 | 3.69 | 4.66 | 51.78 | 3.37 | 4.83 |
| 3 | 2-Cl | 5-Cl | 123°C.–125°C. | 52.02 | 3.69 | 4.66 | 52.09 | 3.66 | 4.78 |
| 4 | 2-Cl | 4-Cl | 174°C.–175°C. | 52.02 | 3.69 | 4.66 | 52.26 | 3.60 | 4.95 |
| 5 | 2-F | H | 124°C.–125°C. | 62.67 | 4.82 | 5.62 | 63.17 | 4.83 | 5.70 |
| 6 | 3-F | H | 84°C.–85°C. | 62.67 | 4.82 | 5.62 | 63.34 | 4.86 | 5.28 |
| 7 | 4-F | H | 110°C.–111°C. | 62.67 | 4.82 | 5.62 | 62.39 | 4.83 | 5.62 |
| 8 | 4-Br | H | 104°C.–105°C. | 50.34 | 3.90 | 4.52 | 50.38 | 3.93 | 4.70 |
| 9 | 4-CH$_3$ | H | 113°C.–114°C. | 68.55 | 6.17 | 5.71 | 68.28 | 6.33 | 5.44 |
| 10 | 2-C$_2$H$_5$ | H | 78°C.–80°C. | 69.48 | 6.61 | 5.40 | 69.62 | 6.76 | 5.23 |

Table I-continued

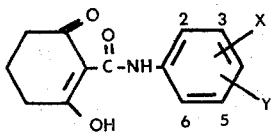

| Example | Substituents X | Y | Melting Point | Calculated C | H | N | Found C | H | N |
|---|---|---|---|---|---|---|---|---|---|
| 11 | 2-CH₃ | 3-Cl | 121°C.–122°C. | 60.11 | 5.04 | 5.01 | 60.11 | 5.02 | 5.01 |
| 12 | 2-CH₃ | 4-Cl | 155°C.–156°C. | 60.11 | 5.04 | 5.01 | 60.19 | 5.04 | 4.79 |
| 13 | 3-Cl | 4-CH₃ | 108°C.–109°C. | 60.11 | 5.04 | 5.01 | 59.99 | 5.18 | 4.95 |
| 14 | 2-CH₃ | 4-Br | 158°C.–159°C. | 51.87 | 4.35 | 4.32 | 52.08 | 4.38 | 4.27 |
| 15 | 4-I | H | 122°C.–123°C. | 43.72 | 3.39 | 3.92 | 43.82 | 3.40 | 3.83 |
| 16 | 4-CH₃S | H | 99°C.–100°C. | 60.62 | 5.45 | 5.05 | 60.45 | 5.40 | 5.21 |
| 17 | 2-CF₃ | H | 85°C.–86°C. | 56.19 | 4.04 | 4.68 | 56.17 | 3.99 | 4.55 |
| 18 | 3-CF₃ | H | 102°C.–103°C. | 56.19 | 4.04 | 4.68 | 56.32 | 4.18 | 4.67 |
| 19 | 3-CF₃ | 5-CF₃ | 119°C.–121°C. | 49.06 | 3.02 | 3.81 | 49.52 | 3.05 | 3.25 |

EXAMPLE 20

Preparation of
2'-Fluoro-2-Hydroxy-6-Oxo-1-Cyclohexene-1-Carboxanilide

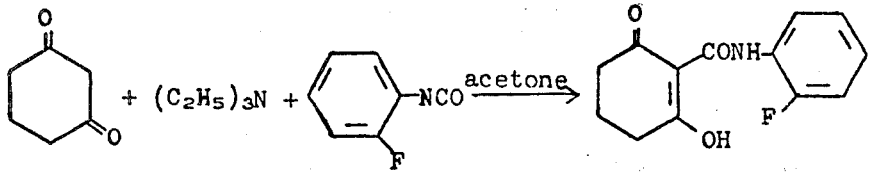

To 6.0 grams of 1,3-cyclohexanedione (0.054 mole) and 5.9 grams of triethylamine (0.059 mole) dissolved in 150 ml. of dry acetone, is added 7.4 grams of o-fluorophenylisocyanate (0.054 mole). The mixture is heated to reflux until none of the isocyanate is visible by infrared spectrophotometry (requires 1 to 3 hour). The orange solution is concentrated, and taken up in chloroform. The chloroform is washed with a dilute aqueous solution of hydrochloric acid, and is dried with magnesium sulfate. Concentration by evaporation yielded 5.0 grams of gummy orange solids. Recrystallization from cyclohexane yields 4.0 grams of the desire product in the form of white crystals; melting point 124°C.–125.5°C. Infrared spectrophotometry and nuclear magnetic resonance spectrometry confirm the structural assignment of the product as 2'-fluoro-2-hydroxy-6-oxo-cyclohexene-1-carboxanilide.

A solution containing 11.2 parts of cyclohexane-1,3-dione and 16.8 parts of 3-chloro-o-tolylisocyanate in pyridine, 100 parts, is heated at 90°C.–100°C. for two hours and then allowed to cool to room temperature. The resulting light slurry is poured into 350 parts of cold 2-normal hydrochloric acid and the crude product is recovered by filtration. The damp solid is dissolved in 600 parts of ethyl alcohol and filtered from 2.9 parts of insoluble solid. The filtrate is chilled on an ice-water bath to precipitate the desired product, which is then filtered to give 17.1 parts of pale buff platelets, melting point 120.5°C.–121.5°C.

Analysis Calculated for C₁₄H₁₄ClNO₃: C, 60.11 H, 5.04; Cl, 12.68; N, 5.01. Found: C, 60.11; H, 5.02; Cl, 12.75; N, 5.01.

EXAMPLES 22–43

Preparation of
4'-Chloro-2-Hydroxy-6-Oxo-1-Cyclohexene-1-Carboxanilide and Related Compounds

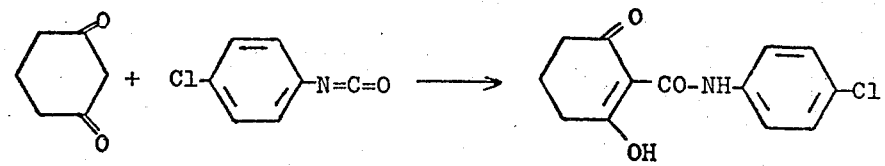

EXAMPLE 21

Preparation of
3'-Chloro-2-Hydroxy-6-Oxo-1-Cyclohexene-1-Carboxy-o-Toluidide

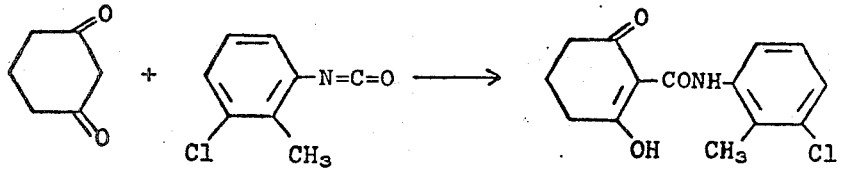

A solution containing 8.5 parts of cyclohexane-1,3-dione, 11.5 parts of p-chlorophenylisocyanate and 7.6 parts of triethylamine in 200 parts of acetone is stirred and refluxed for two hours. The infrared spectrum then shows no isocyanate (band at 2270 cm$^{-1}$). The solution is concentrated under reduced pressure to about 50 parts, with separation of a few crystals, and poured with stirring into 500 parts of 2-normal hydrochloric acid. The precipitated solid is collected by filtration and dried. The resulting solid is mixed with chloroform, 250 parts by volume, and filtered from 6.5 parts of insoluble by-product. Removal of chloroform from the filtrate leaves a light pink solid which is crystallized from alcohol to give 6.7 parts of nearly white solid, melting point 113°C.–114°C.

Analysis Calculated for $C_{13}H_{12}ClNO_3$: C, 58.76; H, 4.56; Cl, 13.34; N, 5.27. Found: C, 58.74; H, 4.55; Cl, 13.16; N, 4.97.

The same product is obtained as a light red powder when the reaction is run in pyridine. Yield, 11.6 parts of recrystallized product.

The compounds of Table II, having the structure set forth below, are prepared by essentially the same procedure, using the appropriately substituted phenylisocyanates for the p-chlorophenylisocyanate used therein.

TABLE II

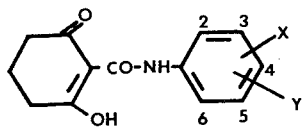

| Example | Substituents X | Y | Melting Point | % Yield |
|---|---|---|---|---|
| 23 | 3-Cl | 4-Cl | 131°C.–132°C. | 62 |
| 24 | 3-Cl | H | 92.5°C.–94°C. | 56 |
| 25 | 4-Cl | H | 113°C.–114°C. | 58 |
| 26 | 4-Cl | 2-CH$_3$ | 155°C.–156°C. | 49 |
| 27 | 2-Cl | 4-NO$_2$ | 267°C.–267.5°C. | 43 |
| 28 | 3-Cl | 4-CH$_3$ | 108°C.–109°C. | 20 |
| 29 | 4-I | H | 122°C.–123°C. | 54 |
| 30 | 4-Br | 2-CH$_3$ | 158°C.–159°C. | 42 |
| 31 | 2-Cl | 4-Cl | 174°C.–175.5°C. | 38 |
| 32 | 4-CH$_3$ | H | 112.5°C.–114°C. | 44 |
| 33 | 2-C$_2$H$_5$ | H | 78°C.–80°C. | 34 |
| 34 | 4-Br | H | 104°C.–105°C. | 44 |
| 35 | 4-F | H | 110°C.–111°C. | 47 |
| 36 | 4-SCH$_3$ | H | 99°C.–100°C. | 43 |
| 37 | 2-CF$_3$ | H | 84.5°C.–85.5°C. | 60 |
| 38 | 3-CF$_3$ | H | 102°C.–103°C. | 75 |
| 39 | 3-F | H | 84°C.–84.5°C. | 62 |
| 40 | 3-CF$_3$ | 5-CF$_3$ | 119°C.–121°C. | 36 |
| 41 | 4-Cl | 3-NO$_2$ | 149.5°C.–150.5°C. | 66 |
| 42 | 3-Cl | 2-CH$_3$ | 120.5°C.–121.5°C. | 61 |
| 43 | 4-O—CO—CH$_3$ | H | 160.5°C.–161.5°C. | 40 |

EXAMPLES 44–53

Insecticidal Activity

The efficacy of the compounds of the present invention for controlling insects is demonstrated by the following tests, wherein aphids and armyworms are used as test species. The procedures employed are as follows. Results obtained are reported in Table III.

Southern Armyworm (*Prodenia eridania* Cram.)

Compounds to be tested are made up as 0.1% solutions in a 65% acetone — 35% water mixture. Sieva lima bean leaves are dipped in the test solution and set in the hood to dry. When dry, they are placed in four-inch petri dishes which have a moist filter paper in the bottom, and then third-instar armyworm larvae about ⅜ inch long are added to each dish. The dishes are covered and held at 80°F., 60% R.H. After 2 days, mortality counts and estimates of the amount of feeding are made.

Nasturtium Aphids (*Aphis rumicis* L.)

The compounds to be tested are made up as 0.1% solutions in a 65% acetone — 35% water mixture. Three-inch pots containing a nasturtium plant two inches tall and infested two days before are selected for testing. The pots are placed on a turntable (4 RPM) and sprayed for two revolutions with an atomizer at 20 psi. air pressure. The spray tip is held about six inches from the plants and the spray is directed so as to give complete coverage of the aphids and the plants. The sprayed plants are laid on their side on white enamel trays which have had the edges coated with oil as a barrier. Mortality estimates are made after holding for two days at 70°F.

TABLE III

| Example | Compound | % Mortality Southern Armyworm | % Mortality Nasturtium Aphids |
|---|---|---|---|
| 44 | (structure: cyclohexenone-CO-NH-phenyl with 3-Cl, 4-Cl, OH) | 100 | 90 |
| 45 | (structure: cyclohexenone-CO-NH-phenyl with 2-Cl, 4-Cl, OH) | 40 | 95 |

TABLE III-continued

| Example | Compound | % Mortality Southern Army-worm | Nasturtium Aphids |
|---|---|---|---|
| 46 | 2-hydroxy-6-oxo-cyclohex-1-ene-carboxylic acid (2-fluorophenyl)amide | 100 | 100 |
| 47 | 2-hydroxy-6-oxo-cyclohex-1-ene-carboxylic acid (3-chlorophenyl)amide | 70 | 100 |
| 48 | 2-hydroxy-6-oxo-cyclohex-1-ene-carboxylic acid (4-chlorophenyl)amide | 100 | 100 |
| 49 | 2-hydroxy-6-oxo-cyclohex-1-ene-carboxylic acid (2-methyl-4-chlorophenyl)amide | 90 | 98 |
| 50 | 2-hydroxy-6-oxo-cyclohex-1-ene-carboxylic acid (4-iodophenyl)amide | 90 | 98 |
| 51 | 2-hydroxy-6-oxo-cyclohex-1-ene-carboxylic acid (2-methyl-4-bromophenyl)amide | 60 | 100 |
| 52 | 2-hydroxy-6-oxo-cyclohex-1-ene-carboxylic acid (2,4-dichlorophenyl)amide | 100 | 100 |
| 53 | 2-methyl-6-oxo-cyclohex-1-ene-carboxylic acid (4-methylphenyl)amide | 0 | 100 |

EXAMPLES 54–59

The efficacy of the compounds of the present invention against spider mites is demonstrated in the following tests using the procedure set forth below. The results achieved are shown in Table IV below.

Two-Spotted Spider Mite (*Tetranychus telarius* L.)

Compounds to be tested are made up as 0.1% solutions in a 65% acetone — 35% water mixture. Sieva lima bean plants with the first pair of leaves 3 to 4 inches in size are infested about 5 hours before testing, using about 100 to 200 adult mites per leaf. The infested leaves are dipped in the test solutions (in four-inch crystallizing dishes) for 3 seconds, and the plants set in the hood to dry. The treated plants are held for two days at 80°F., 60% R.H., and the adult mite mortality calculated by counting dead and alive adults on one leaf under the 10X binocularscope. The other leaf is held an additional 5 days and then is examined at 10X power to estimate the kill of eggs and newly-hatched nymphs, giving a measure of ovocidal and residual action, respectively.

TABLE IV

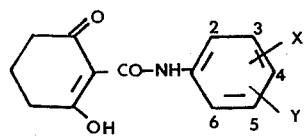

| Example | Substituents | % Mortality Spider Mites |
|---|---|---|
| 54 | 3,4-di-Cl | 100 |
| 55 | 3,6-di-Cl | 100 |
| 56 | 3-Cl | 100 |
| 57 | 4-Cl | 100 |
| 58 | 4-I | 100 |
| 59 | 2,4-di-Cl | 50 |

EXAMPLES 60–78

Effective control of acarina larvae is demonstrated in the following tests with larvae of *Boophilus microplus*, a one-host tick which can remain on a single host through its three life stages, i.e., larvae, nymph and adult. In these tests, a 10% acetone — 90% water mixture contains from 1.0 to 100 ppm. of test compound. Twenty larvae are enclosed in a pipet sealed at one end with a gauze material and solution containing the test compound is then drawn through the pipet with a vacuum hose simulating a spray system. The ticks are then held for 48 hours at room temperature and mortality is determined. The results achieved are set forth in Table V below.

TABLE V

| Example | X | Y | % Mortality | ppm of Active Ingredient |
|---|---|---|---|---|
| 60 | 2-Cl | 4-Cl | 80 | 1.0 |
| 61 | 3-Cl | 4-Cl | 100 | 10.0 |
|    |      |      | 100 | 3.3 |
| 62 | 2-Cl | 5-Cl | 100 | 10.0 |
| 63 | 4-Cl | 2-CH₃ | 100 | 10.0 |
| 64 | 3-Cl | 4-CH₃ | 100 | 10.0 |
| 65 | 4-Cl | 3-NO₂ | 80 | 33.0 |
| 66 | 5-Cl | 6-CH₃ | 100 | 3.3 |
| 67 | 4-Br | H | 80 | 33.0 |
| 68 | 4-Br | 2-CH₃ | 100 | 3.3 |
| 69 | 4-I | H | 100 | 10.0 |
| 70 | 3-F | H | 80 | 3.3 |
| 71 | 4-F | H | 100 | 33.0 |
| 72 | 2-CF₃ | H | 100 | 33.0 |
| 73 | 3-CF₃ | H | 100 | 33.0 |
|    |       |   | 100 | 33.0 |
| 74 | 3-CF₃ | 5-CF₃ | 100 | 10.0 |
| 75 | 4-CH₃ | H | 80 | 33.0 |
| 76 | 2-C₂H₅ | H | 100 | 100.0 |
|    |        |   | 100 | 50.0 |
| 77 | 4-SCH₃ | H | 100 | 33.0 |
| 78 | H | H | 100 | 100.0 |
|    |   |   | 100 | 50.0 |

EXAMPLES 79–82

The efficacy of the compounds of the invention for controlling acarine nymphs is demonstrated following the same procedure used in Example 60, but substituting 10 nymphs of the three-host tick, *Amblyomma americanum*, for the 20 *Boophilus* larvae. Compounds are tested at from 10 ppm to 100 ppm of active ingredient in 10% acetone aqueous solution. The results achieved are reported in Table VI below.

TABLE VI

| Example | X | Y | % Mortality | ppm of Active Ingredient |
|---|---|---|---|---|
| 79 | 3-Cl | 4-Cl | 100 | 10 |
| 80 | 3-Cl | H | 100 | 33 |
| 81 | 4-Cl | H | 100 | 10 |
| 82 | 2-F | H | 70 | 100 |

EXAMPLES 83–96

Efficacy of the compounds of the present invention for the control of adult ticks is demonstrated in the following tests wherein adult *Boophilus microplus* ticks which have dropped from cattle are collected and used for testing.

Compound to be tested is dissolved in a 35% acetone — 65% water mixture in sufficient amount to provide from about 40 to 2000 ppm of compound in the test solution. Ten ticks per treatment are used and they are immersed in test solution for 3 to 5 minutes, then removed and placed in cages and held at room temperature for three days. Mortality counts are then made and recorded. For these tests, non-resistant ticks as well as ethion-resistant and dioxathion-resistant ticks are used since the latter two are among the most difficult of their kind to control. Results of these tests are given in Table VII below.

EXAMPLES 102–139

Preparation of Dioxocyclohexanecarboxanilides

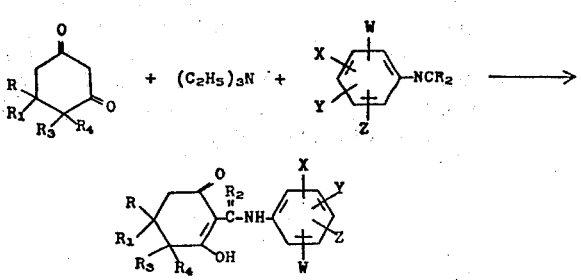

TABLE VII

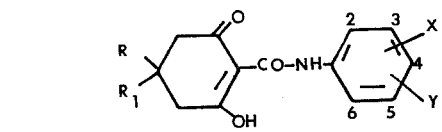

| | Substituents | | | ppm of Active | % Mortality Ethion | Dioxathion | Non- |
| Ex. | R | $R_1$ | X | Y | Ingredient | Resistant | Resistant | Resistant |
|---|---|---|---|---|---|---|---|---|
| 83 | H | H | 3-Cl | H | 2000 | 80 | 50 | — |
| 84 | H | H | 4-Cl | H | 1000 | 100 | 100 | — |
| | | | | | 500 | 20 | 50 | — |
| 85 | H | H | 3-Cl | 4-$CH_3$ | 2000 | 50 | 10 | — |
| 86 | H | H | 3-Cl | 4-Cl | 1900 | 100 | 100 | — |
| | | | | | 800 | 50 | 100 | — |
| | | | | | 40 | 10 | 40 | — |
| 87 | $CH_3$ | $CH_3$ | H | H | 2000 | 90 | 80 | — |
| 88 | H | H | 3-Cl | H | 1000 | — | — | 100 |
| 89 | H | H | 4-Cl | H | 1000 | — | — | 100 |
| 90 | H | H | 3-Cl | 4-Cl | 330 | — | — | 100 |
| | | | | | 100 | — | — | 10 |
| 91 | H | H | 4-Cl | 2-$CH_3$ | 1000 | — | — | 100 |
| 92 | H | H | 3-Cl | 4-$CH_3$ | 1000 | — | — | 100 |
| 93 | H | H | 2-Cl | 3-Cl | | | | No test |
| 94 | $CH_3$ | $CH_3$ | 2-Cl | 3-Cl | | | | No test |
| 95 | H | H | p-oMe | H | | | | No test |
| 96 | $CH_3$ | $CH_3$ | p-oMe | H | | | | No test |

EXAMPLES 97–101

Following the procedures set forth in Examples 60 through 78 and 79 through 82 above, the following data were obtained.

wherein $R_2$ is O or S

Following the procedure of Example 20, equimolar quantities (0.064 moles) of the appropriate dione, isocyanate or isothiocyanate and triethylamine in 160 ml.

TABLE VIII

| | Substituents | | | | ppm. of Active | *Boophilus microplus* | *Amblyomma americanum* |
| Example | R | $R_1$ | X | Y | Ingredient | (larvae) | Nymphs |
|---|---|---|---|---|---|---|---|
| 97 | $CH_3$ | $CH_3$ | H | H | 20 | — | 100 |
| 98 | H | H | 2-Cl | 3-Cl | 10 | 100 | — |
| 99 | $CH_3$ | $CH_3$ | 2-Cl | 3-Cl | 80 | 100 | — |
| 100 | H | H | p-$OCH_3$ | H | 100 | 100 | — |
| 101 | $CH_3$ | $CH_3$ | p-$OCH_3$ | H | 100 | 100 | — | of dry acetone are heated at reflux for about 9 hours. The mixture is filtered and the filtrate is poured on ice and stirred to afford a first crop of the carboxanilide. This is then collected and the filtrate is acidified to pH 4 with concentrated hydrochloric acid to afford a second crop, which is collected. The combined crops are then recrystallized from appropriate solvents such as alcohols, alcohol-water, or acetone. Compounds prepared by this procedure are listed in Table IX below by structure with their melting points and recrystallization solvents.

TABLE IX

| Example Number | Structure | Melting Point °C. | Recrystallization Solvent |
|---|---|---|---|
| 102 | (2-oxocyclohexyl-1-ene-OH)-CONH-naphthyl | 142.5–143.5 | Acetone |
| 103 | (2-oxocyclohexyl-1-ene-OH)-CONH-C6H4-NO2 | 227–228 | Acetone |
| 104 | (2-oxocyclohexyl-1-ene-OH)-CONH-C6H4-CH3 | — | — |
| 105 | (2-oxocyclohexyl-1-ene-OH)-CSNH-C6H5 | 78–80 | Hexane |
| 106 | (2-oxocyclohexyl-1-ene-OH)-CO-NH-C6H4-OCH3 | 94.5–97 | 95% EtOH |
| 107 | (5,5-dimethyl-2-oxocyclohexyl-1-ene-OH)-CO-NH-C6H4-OCH3 | 101–104 | 95% EtOH |
| 108 | (2-oxocyclohexyl-1-ene-OH)-CO-NH-C6H3-Cl2 | 120–124 | 95% EtOH |

TABLE IX-continued

| Example Number | Structure | Melting Point °C. | Recrystallization Solvent |
|---|---|---|---|
| 109 | 4,4-dimethyl-cyclohexane-1,3-dione-2-CO-NH-(2,3-dichlorophenyl) | 157–159.5 | Me$_2$CO/-95% EtOH |
| 110 | cyclohexane-1,3-dione-2-CO-NH-(2-chlorophenyl) | 116.5–119 | 95% EtOH |
| 111 | cyclohexane-1,3-dione-2-CS-NH-(3-fluorophenyl) | 114–116.5 | 95% EtOH ether |
| 112 | cyclohexane-1,3-dione-2-CS-NH-(4-fluorophenyl) | 95–97 | 95% EtOH |
| 113 | 4,4-dimethyl-cyclohexane-1,3-dione-2-CO-NH-(2-chlorophenyl) | 109–111 | MeOH ether |
| 114 | cyclohexane-1,3-dione-2-CO-NH-(2-methoxyphenyl) | 122–125 | MeOH |
| 115 | 4,4-dimethyl-cyclohexane-1,3-dione-2-CO-NH-(2-methoxyphenyl) | 148–150.5 | MeOH |
| 116 | 4,4-dimethyl-cyclohexane-1,3-dione-2-CO-NH-(3-chlorophenyl) | 86.5–88.5 | 95% EtOH |
| 117 | 4,4-dimethyl-cyclohexane-1,3-dione-2-CO-NH-(2-methyl-3-chlorophenyl) | 155–157.5 | 95% EtOH |
| 118 | 4,4-dimethyl-cyclohexane-1,3-dione-2-CO-NH-(2,5-dichlorophenyl) | 143–146 | 95% EtOH |

TABLE IX-continued

| Example Number | Structure | Melting Point °C. | Recrystallization Solvent |
|---|---|---|---|
| 119 | 4,4-dimethyl-cyclohexanedione with CO-NH-(3-Cl, 4-CH₃ phenyl) | 93.5–96 | 95% EtOH |
| 120 | 4,4-dimethyl-cyclohexanedione with CO-NH-(2,4-diCl phenyl) | 154–156 | 95% EtOH |
| 121 | cyclohexanedione with CO-NH-(2-CH₃, 5-Cl phenyl) | 140–143 | 95% EtOH |
| 122 | cyclohexanedione with CO-NH-(2,6-diCl phenyl) | 212–215 | Me₂CO/95% EtOH |
| 123 | 4,4-dimethyl-cyclohexanedione with CO-NH-(2,6-diCl phenyl) | 203–205.5 | Me₂CO |
| 124 | cyclohexanedione with CO-NH-(2,5-diCH₃ phenyl) | 129.5–132 | MeOH |
| 125 | 4,4-dimethyl-cyclohexanedione with CO-NH-(2,5-diCH₃ phenyl) | 117–120 | MeOH |
| 126 | 4,4-dimethyl-cyclohexanedione with CO-NH-(2,5-diCH₃ phenyl) | 157–159 | 95% EtOH |
| 127 | cyclohexanedione with CO-NH-(3,5-diCl phenyl) | 183–186.5 | Me₂CO |

TABLE IX-continued

| Example Number | Structure | Melting Point °C. | Recrystallization Solvent |
|---|---|---|---|
| 128 | 2-hydroxy-6-oxocyclohex-1-enyl-CO-NH-(2-Cl,4-CH₃-phenyl) | 147–149.5 | 95% EtOH |
| 129 | 4,4-dimethyl-2-hydroxy-6-oxocyclohex-1-enyl-CO-NH-(3,5-diCl-phenyl) | 118.5–120.5 | 95% EtOH |
| 130 | 4,4-dimethyl-2-hydroxy-6-oxocyclohex-1-enyl-CO-NH-(2-Cl,4-CH₃-phenyl) | 148.5–150.5 | 95% EtOH |
| 131 | 2-hydroxy-6-oxocyclohex-1-enyl-CO-NH-(2-Cl,6-CH₃-phenyl) | 153–156 | 95% EtOH |
| 132 | 4,4-dimethyl-2-hydroxy-6-oxocyclohex-1-enyl-CO-NH-(3-CF₃-phenyl) | 114–115.5 | 95% EtOH |
| 133 | 2-hydroxy-6-oxocyclohex-1-enyl-CO-NH-(2,4,6-triCl-phenyl) | 167–170 | 95% EtOH |
| 134 | 2-hydroxy-6-oxocyclohex-1-enyl-CO-NH-(2,4,6-triCl-phenyl) | 174–177 | 95% EtOH |
| 135 | 4,4-dimethyl-2-hydroxy-6-oxocyclohex-1-enyl-CO-NH-(2,4,6-triCl-phenyl) | 144–147 | MeOH |
| 136 | 4,4-dimethyl-2-hydroxy-6-oxocyclohex-1-enyl-CO-NH-(2-Cl,6-CH₃-phenyl) | 151–153 | 95% EtOH |
| 137 | 4,4-dimethyl-2-hydroxy-6-oxocyclohex-1-enyl-CO-NH-(2,6-diCl-phenyl) | 184–187 | Me₂CO |

TABLE IX-continued

| Example Number | Structure | Melting Point °C. | Recrystal- lization Solvent |
|---|---|---|---|
| 138 | (4-phenyl-2-hydroxy-6-oxo-cyclohex-1-enyl)-CO-NH-(2,4-dichlorophenyl) | 157.5– 159 | 2B EtOH |
| 139 | (4,4-dimethyl-2-hydroxy-6-oxo-cyclohex-1-enyl)-CS-NH-(4-chlorophenyl) | 138–141 | MeOH |

EXAPLES 140–171

Preparation of Dioxocyclohexanecarboxanilides

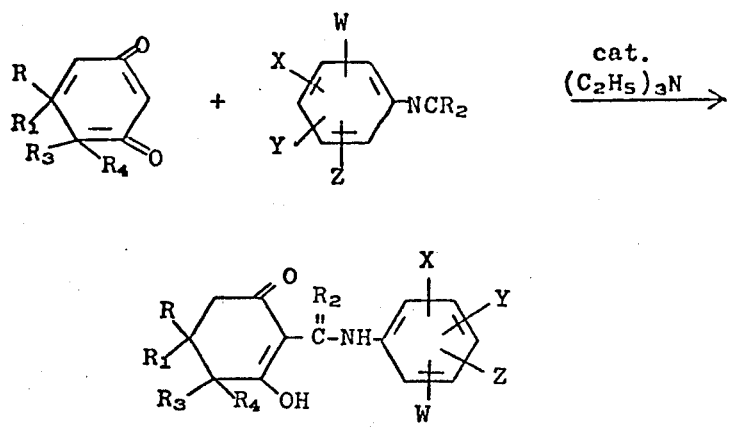

wherein $R_2$ is O or S

The dione (0.03 mole) is dissolved or suspended in 25 ml. of dry methyl ethyl ketone and stirred. The isocyanate or isothiocyanate (0.033 mole or 10% excess) is dissolved in 4 ml. of methyl ethyl ketone and added to the mixture. To this is added a catalytic amount (about two drops) of triethylamine. The mixture is then refluxed for about 2 hours and cooled to afford the carboxanilide, which is collected and washed with ethyl ether. Occasionally, the product will not crystallize from the reaction mixture, and hence, the mixture is evaporated to dryness to afford the crude carboxanilide. The product is then recrystallized from appropriate solvents such as alcohols, alcohol-water mixtures, or acetone. Compounds prepared by this procedure are listed in Table X below by structure with their melting points and recrystallization solvents.

TABLE X

| Example Number | Structure | Melting Point °C. | Recrystal- lization Solvent |
|---|---|---|---|
| 140 | (2-hydroxy-6-oxo-cyclohex-1-enyl)-CO-NH-(2,4,5-trichlorophenyl) | 233–236 dec. | DMF |
| 141 | (4,4-dimethyl-2-hydroxy-6-oxo-cyclohex-1-enyl)-CO-NH-(2,4,5-trichlorophenyl) | 175.5– 179 | 95% EtOH |

TABLE X-continued

| Example Number | Structure | Melting Point °C. | Recrystallization Solvent |
|---|---|---|---|
| 142 | (4,4-dimethyl cyclohexanedione with CO-NH-(2-Cl,5-CH3-phenyl)) | 137.5–139 | 95% EtOH |
| 143 | (cyclohexanedione with CO-NH-(2-Cl,5-CH3-phenyl)) | 126–131 | 95% EtOH |
| 144 | (cyclohexanedione with CO-NH-(2,3,4-trichlorophenyl)) | 183–184 | 2B EtOH |
| 145 | (4-methyl cyclohexanedione with CO-NH-phenyl) | 98.5–101 | 95% EtOH |
| 146 | (4-phenyl cyclohexanedione with CO-NH-phenyl) | 127.5–130 | 95% EtOH |
| 147 | (4-phenyl cyclohexanedione with CO-NH-(4-Cl-phenyl)) | 155–160 | Me$_2$CO |
| 148 | (4-phenyl cyclohexanedione with CO-NH-(3,4-dichlorophenyl)) | 129–134 | 2B EtOH |
| 149 | (4,4-dimethyl cyclohexanedione with CO-NH-(2,3,4-trichlorophenyl)) | 198–200 | EtOAc |

TABLE X-continued

| Example Number | Structure | Melting Point °C. | Recrystallization Solvent |
|---|---|---|---|
| 150 | 3-hydroxy-6-oxo-4-phenyl-N-phenyl-cyclohex-2-ene-carboxamide | 105.5–111.5 | MeOH |
| 151 | 4-ethyl-3-hydroxy-6-oxo-N-(4-chlorophenyl)-cyclohex-2-ene-carboxamide | 76–78 | 95% EtOH |
| 152 | 4-ethyl-3-hydroxy-6-oxo-N-(4-chloro-2-methylphenyl)-cyclohex-2-ene-carboxamide | 86–93 | MeOH |
| 153 | 4-(4-chlorophenyl)-3-hydroxy-6-oxo-N-(4-chlorophenyl)-cyclohex-2-ene-carboxamide | 147–150 | $Me_2CO$ |
| 154 | 4-methyl-3-hydroxy-6-oxo-N-(4-chloro-2-methylphenyl)-cyclohex-2-ene-carboxamide | 191–194.5 | EtOAC |
| 155 | 3-hydroxy-6-oxo-4-phenyl-N-(2,4-dichlorophenyl)-cyclohex-2-ene-carboxamide (tautomer) | 131–134.5 | 2B EtOH |
| 156 | 4-methyl-3-hydroxy-6-oxo-N-(2,4-dichlorophenyl)-cyclohex-2-ene-carboxamide | 180.5–182.5 | 2B EtOH |
| 157 | 3-hydroxy-6-oxo-4-phenyl-N-(4-chloro-2-methylphenyl)-cyclohex-2-ene-carboxamide | 129–131 | 2B EtOH |

TABLE X-continued

| Example Number | Structure | Melting Point °C. | Recrystallization Solvent |
|---|---|---|---|
| 158 | 4-Cl-C₆H₄-(cyclohexenone-OH)-CO-NH-C₆H₃(Cl)(Cl) (3,4-diCl) | 163–165 | Me₂CO |
| 159 | C₆H₅-(cyclohexenone-OH)-CO-NH-C₆H₃(Cl)(CH₃) | 148–151 | 2B EtOH |
| 160 | C₆H₅-CH₂-(cyclohexenone-OH)-CO-NH-C₆H₃(Cl)(Cl) | 175.5–177.5 | EtOAc |
| 161 | 4-Cl-C₆H₄-(cyclohexenone-OH)-CO-NH-C₆H₃(Cl)(CH₃) | 170.5–173.5 | Me₂CO |
| 162 | 4-Cl-C₆H₄-(cyclohexenone-OH)-CO-NH-C₆H₅ | 130.5–133.5 | 95% EtOH |
| 163 | 4-Cl-C₆H₄-(cyclohexenone-OH)-CO-NH-C₆H₃(Cl)(Cl) (2,4-diCl) | 166.5–168 | Me₂CO |
| 164 | C₂H₅-(cyclohexenone-OH)-CO-NH-C₆H₃(Cl)(Cl) | 81–90 | MeOH |
| 165 | C₆H₅-CH₂-(cyclohexenone-OH)-CO-NH-C₆H₄-Cl | 154.5–156 | Me₂CO |
| 166 | C₆H₅-CH₂-(cyclohexenone-OH)-CO-NH-C₆H₄-Cl (2-Cl) | 140–141.5 | Me₂CO |

TABLE X-continued

| Example Number | Structure | Melting Point °C. | Recrystallization Solvent |
|---|---|---|---|
| 167 | (2-oxocyclohex-1-en-1-yl, 3-OH)-CS-NH-C6H4-Cl | 106–110 | 95% EtOH ether |
| 168 | 5-CH3-(2-oxocyclohex-1-en-1-yl, 3-OH)-CO-NH-C6H4-Cl | 122–123.5 | EtOH |
| 169 | 5-CH3-(2-oxocyclohex-1-en-1-yl, 3-OH)-CO-NH-C6H3-Cl2 | 126.5–128.5 | Acetone |
| 170 | 5-phenyl-(2-oxocyclohex-1-en-1-yl, 3-OH)-CO-NH-C6H3-Cl2 | 135–136 | Acetone |
| 171 | 5-phenyl-(2-oxocyclohex-1-en-1-yl, 3-OH)-CO-NH-C6H4-Cl | 148–150 | Acetone |

EXAMPLES 172–211

Effective control of acarina larvae is demonstrated in the following tests with larvae of *Boophilus microplus*, a one-host tick which can remain on a single host through its three life stages, i.e., larvae, nymph and adult. In these tests, a 10% acetone — 90% water mixture contains from 1.0 to 100 ppm. of test compound. Twenty larvae are enclosed in a pipet sealed at one end with a gauze material and solution containing the test compound is then drawn through the pipet with a vacuum hose simulating a spray system. The ticks are then held for 48 hours at room temperature and mortality is determined. The results achieved are set forth in Table XI below.

TABLE XI

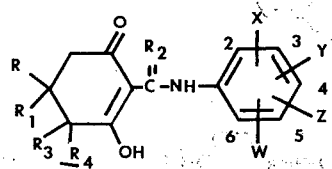

| Example Number | R | $R_1$ | $R_2$ | $R_3$ | $R_4$ | W | X | Y | Z | ppm. Active Ingredient | % Mortality |
|---|---|---|---|---|---|---|---|---|---|---|---|
| 172 | H | H | O | H | H | H | —OCH3 (4) | H | H | 100 | 100 |
| 173 | CH3 | CH3 | O | H | H | H | —OCH3 (4) | H | H | 100 | 100 |
| 174 | H | H | O | H | H | Cl (6) | H | H | Cl (5) | 10 | 100 |
| 175 | CH3 | CH3 | O | H | H | Cl (6) | H | H | Cl (5) | 33 | 80 |
| 176 | H | H | O | H | H | H | benzo (5–6) | | H | 33 | 80 |
| 177 | H | H | O | H | H | Cl (6) | H | H | H | 33 | 100 |
| 178 | H | H | S | H | H | H | H | H | F (5) | 100 | 100 |
| 179 | H | H | S | H | H | H | H | F (4) | H | 100 | 100 |
| 180 | CH3 | CH3 | O | H | H | Cl (6) | H | H | H | 33 | 100 |
| 181 | H | H | O | H | H | H | —OCH3 (6) | H | H | 100 | 100 |
| 182 | CH3 | CH3 | O | H | H | H | H | H | Cl (5) | 33 | 100 |

TABLE XI-continued

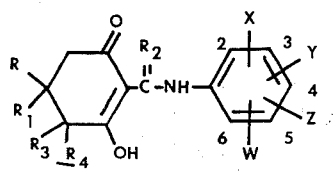

| Example Number | R | $R_1$ | $R_2$ | $R_3$ | $R_4$ | W | X | Y | Z | ppm. Active Ingredient | % Mortality |
|---|---|---|---|---|---|---|---|---|---|---|---|
| 183 | $CH_3$ | $CH_3$ | O | H | H | H | H | $CH_3$ (6) | Cl (5) | 33 | 100 |
| 184 | $CH_3$ | $CH_3$ | O | H | H | H | $CH_3$ (4) | Cl (5) | Cl (5) | 33 | 100 |
| 185 | $CH_3$ | $CH_3$ | O | H | H | Cl (6) | H | Cl (4) | H | 3.3 | 100 |
| 186 | H | H | O | H | H | H | H | $CH_3$ (6) | Cl (3) | 100 | 80 |
| 187 | H | H | O | H | H | H | $CH_3$ (6) | $CH_3$ (3) | H | 33 | 100 |
| 188 | $CH_3$ | $CH_3$ | O | H | H | H | $CH_3$ (6) | $CH_3$ (3) | H | 100 | 50 |
| 189 | H | H | O | H | H | H | Cl (5) | Cl (3) | H | 10 | 100 |
| 190 | H | H | O | H | H | Cl (6) | H | $CH_3$ (4) | H | 33 | 100 |
| 191 | $CH_3$ | $CH_3$ | O | H | H | Cl (6) | Cl (5) | Cl (3) | Cl (2) | 100 | 20 |
| 192 | H | H | O | H | H | H | $CH_3$ (5) | H | Cl (2) | 10 | 100 |
| 193 | H | H | O | H | H | Cl (6) | Cl (5) | Cl (4) | Cl (3) | 3.3 | 100 |
| 194 | $CH_3$ | H | O | H | H | H | H | H | H | 33 | 100 |
| 195 | phenyl | H | O | H | H | H | H | H | H | 3.3 | 100 |
| 196 | H | H | O | phenyl | H | H | H | Cl (5) | Cl (4) | 100 | 100 |
| 197 | $CH_3$ | $CH_3$ | O | H | H | Cl (6) | Cl (5) | Cl (4) | Cl (3) | 100 | 50 |
| 198 | H | phenyl | O | H | H | Cl (6) | H | Cl (4) | H | 100 | 100 |
| 199 | H | H | O | H | phenyl | H | H | H | H | 33 | 100 |
| 200 | H | H | O | $C_2H_5$ | H | H | H | Cl (4) | H | 10 | 100 |
| 201 | H | H | O | $C_2H_5$ | H | H | $CH_3$ (6) | Cl (4) | H | 10 | 100 |
| 202 | 4-Cl-phenyl | H | O | H | H | H | H | Cl (4) | H | 10 | 100 |
| 203 | $CH_3$ | H | O | H | H | H | $CH_3$ (6) | Cl (4) | H | 100 | 80 |
| 204 | $CH_3$ | H | O | H | H | H | Cl (6) | Cl (4) | H | 10 | 100 |
| 205 | H | H | O | phenyl | H | H | $CH_3$ (6) | Cl (4) | H | 33 | 100 |
| 206 | H | H | S | H | H | H | H | Cl (4) | H | 100 | 50 |
| 207 | $CH_3$ | $CH_3$ | S | H | H | H | H | Cl (4) | H | 100 | 50 |
| 208 | $CH_3$ | H | O | H | H | H | H | Cl (4) | H | 10 | 100 |
| 209 | $CH_3$ | H | O | H | H | H | Cl (5) | Cl (4) | H | 1.0 | 100 |
| 210 | phenyl | H | O | H | H | H | Cl (5) | Cl (4) | H | 33 | 80 |
| 211 | phenyl | H | O | H | H | H | H | Cl (4) | H | 10 | 100 |

EXAMPLES 212–225

Mosquito Egg and Larva Test

Test solutions are prepared in 50% acetone — 50% water, initially at 1000 ppm. One ml. of 1000 ppm. solution is pipetted into 249 ml. of water in a 400 ml. beaker to yield a 4.0 ppm. test rate. About 100 eggs, 0 to 24 hours old, from *Anopheles quadrimaculatus* mosquitoes are added inside a wax paper ring floating on the surface of the water. Egg mortality results are noted after two days. Larval mortality results are noted after 3 days. Active compounds are further tested at tenfold dilutions until activity diminishes. The results achieved are set forth in Table XII below.

Ratings:
+ = killed 86% to 100%
± = killed 41% to 85%
0 = killed 0% to 40%
− = not tested

TABLE XII

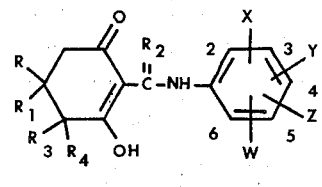

| Example Number | R | $R_1$ | $R_2$ | $R_3$ | $R_4$ | W | X | Y | Z | Mosquito Eggs 4 | .4 | Larvae 4 | .4 |
|---|---|---|---|---|---|---|---|---|---|---|---|---|---|
| 212 | H | H | O | H | H | H | H | Cl (4) | H | + | ± | − | 0 |
| 213 | H | H | O | H | H | H | Cl (2) | Cl (4) | H | 0 | 0 | + | + |
| 214 | H | H | O | H | H | H | Cl (3) | Cl (4) | H | 0 | 0 | + | 0 |
| 215 | H | H | O | H | H | F (5) | H | H | H | ± | 0 | + | 0 |
| 216 | H | H | O | H | H | H | H | F (4) | H | ± | 0 | + | 0 |
| 217 | H | H | O | H | H | H | H | $CH_3$ (6) | Cl (3) | ± | 0 | + | 0 |
| 218 | $CH_3$ | $CH_3$ | O | H | H | H | H | $CH_3$ (4) | Cl (3) | ± | 0 | + | 0 |
| 219 | H | H | O | H | H | H | Cl (3) | Cl (5) | H | + | + | ± | 0 |

TABLE XII-continued

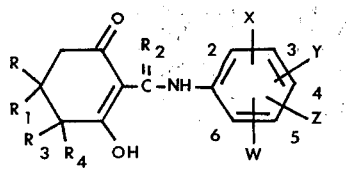

| Example Number | R | $R_1$ | $R_2$ | $R_3$ | $R_4$ | W | X | Y | Z | Mosquito Eggs 4 | | Larvae 4 | |
|---|---|---|---|---|---|---|---|---|---|---|---|---|---|
| | | | | | | | | | | 4 | .4 | 4 | .4 |
| 220 | H | H | O | H | H | Cl (6) | Cl (5) | Cl (4) | Cl (3) | ± | O | + | + |
| 221 | CH$_3$ | CH$_3$ | O | H | H | Cl (6) | Cl (5) | Cl (4) | Cl (3) | + | O | + | |
| 222 | H | H | O | C$_2$H$_5$ | H | H | H | Cl (4) | H | + | | | |
| 223 | CH$_3$ | H | O | H | H | H | H | CH$_3$ (6) | Cl (4) | + | | | |
| 224 | CH$_3$ | H | O | H | H | H | Cl (4) | H | H | + | | | |
| 225 | CH$_3$ | H | O | H | H | H | Cl (5) | Cl (4) | H | + | | | |

Concentration in ppm.

± = killed 41% to 85%
0 = killed 0% to 40%
— = not tested

EXAMPLES 226–232

Budworm Egg and Larva Test

TABLE XIII

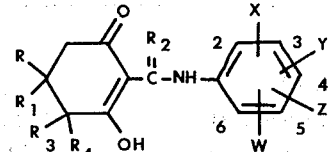

| Example Number | R | $R_1$ | $R_2$ | $R_3$ | $R_4$ | W | X | Y | Z | Budworm Eggs 100 ppm. | Larvae 100 ppm. |
|---|---|---|---|---|---|---|---|---|---|---|---|
| 226 | H | H | O | H | H | H | H | Cl (4) | H | + | — |
| 227 | H | H | O | H | H | H | H | Cl (4) | Cl (3) | + | — |
| 228 | H | H | O | H | H | H | Cl (3) | H | Cl (5) | ± | + |
| 229 | CH$_3$ | H | O | H | H | H | Cl (4) | H | H | + | — |
| 230 | CH$_3$ | H | O | H | H | Cl (5) | Cl (4) | H | H | + | — |
| 231 | H | H | O | C$_2$H$_5$ | H | H | Cl (4) | H | H | + | — |
| 232 | p-Cl-phenyl | H | O | H | H | H | Cl (4) | H | H | + | — |

Test solutions are prepared in 50% acetone — 50% water, initially at 100 ppm. A one-inch square piece of cheesecloth infested with about 100 eggs of *Heliothis virescens* is dipped for a second in the solution along with a young cotton leaf. These are allowed to dry and are placed in a covered wax paper cup. Egg mortality ratings are made after 3 days. Larval mortality ratings are made after seven days. Ratings are as shown below in Table XIII.

Ratings:
+ = killed 86% to 100%

EXAMPLES 233–235

Mite Egg Test

Cotton plants are infested with mites (*Tetranychus urticae*) 4 hours before testing to allow egg laying. Plants are dipped in 1000 ppm. solution in 65% acetone/35% water. Adult mortality is noted after 2 days. Egg mortality or mortality of newly hatched nymphs is noted after 7 days. The results achieved are set forth in Table XIV below.

TABLE XIV

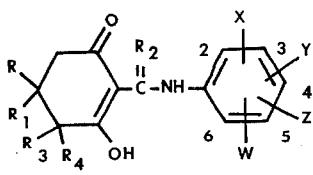

| Example Number | R | $R_1$ | $R_2$ | $R_3$ | $R_4$ | W | X | Y | Z | % Mortality Mite Eggs |
|---|---|---|---|---|---|---|---|---|---|---|
| 233 | H | H | O | H | H | H | Cl (4) | H | H | 100 |
| 234 | H | H | O | H | H | H | Cl (4) | Cl (2) | H | 100 |
| 235 | H | H | O | H | H | H | Cl (4) | H | Cl (3) | 100 |

We claim:

1. A method for the control of pests selected from the group consisting of insects and acarids as well as the eggs or larvae thereof, comprising contacting said insects, acarids, or eggs or larvae thereof with a pesticidally effective amount of a compound having the formula:

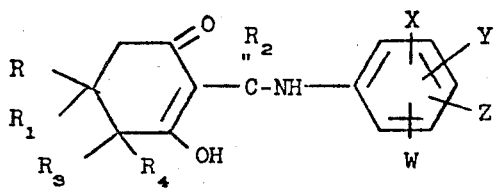

wherein R and $R_1$ are each selected from the group consisting of hydrogen, lower alkyl ($C_1$–$C_4$), phenyl, halophenyl and benzyl; $R_2$ is sulfur or oxygen; $R_3$ and $R_4$ are each selected from the group consisting of hydrogen, lower alkyl ($C_1$–$C_4$) and phenyl; W is hydrogen or halogen; X is hydrogen, halogen, lower aikyl ($C_1$–$C_4$), halo-substituted lower alkyl ($C_1$–$C_4$), lower alkoxy ($C_1$–$C_4$), lower alkylthio ($C_1$–$C_4$) or nitro; Y is hydrogen, halogen, lower alkyl ($C_1$–$C_4$) or halo-lower alkyl ($C_1$–$C_4$) and Z is hydrogen or halogen.

2. The method according to claim 1 where $R_2$ is oxygen.

3. The method according to claim 1 where $R_2$ is sulfur.

4. The method according to claim 2 where R, $R_1$, $R_3$, $R_4$, W, Z and Y are each hydrogen, and X is halogen.

5. The method according to claim 2 where R, $R_1$, $R_3$, $R_4$, W and Z are each hydrogen, and X and Y are halogen.

6. The method according to claim 2 where R, $R_1$, $R_3$, $R_4$, W and Z are each hydrogen, X is halogen, and Y is lower alkyl ($C_1$–$C_4$).

7. The method according to claim 2 wherein eggs or larvae are contacted.

8. The method according to claim 2 where the compound is: 3'-chloro-2-hydroxy-4,4-dimethyl-6-oxo-1-cyclohexene-1-carboxanilide.

9. The method according to claim 2 where the compound is: 3',4'-dichloro-3-ethyl-2-hydroxy-6-oxo-1-cyclohexene-1-carboxanilide.

10. The method according to claim 2 where the compound is: 4'-chloro-2-hydroxy-4-methyl-6-oxo-1-cyclohexene-1-carboxanilide.

11. The method according to claim 2 where the compound is: 4'-chloro-3-ethyl-2-hydroxy-6-oxo-1-cyclohexene-1-carboxanilide.

12. The method according to claim 2 where the compound is: 3',4'-dichloro-2-hydroxy-4-methyl-6-oxo-1-cyclohexene-1-carboxanilide.

13. The method according to claim 2 where the compound is: 4'-bromo-2-hydroxy-6-oxo-1-cyclohexene-1-carboxanilide.

14. The method according to claim 2 where the compound is: 2-hydroxy-4'-iodo-6-oxo-1-cyclohexene-1-carboxanilide.

15. The method according to claim 2 where the compound is: 4'-chloro-2-hydroxy-6-oxo-1-cyclohexene-1-carboxanilide.

* * * * *